United States Patent
Archuleta

(10) Patent No.: US 11,281,855 B1
(45) Date of Patent: Mar. 22, 2022

(54) REINFORCEMENT LEARNING APPROACH TO DECODE SENTENCE AMBIGUITY

(71) Applicant: Michelle Archuleta, Lakewood, CO (US)

(72) Inventor: Michelle Archuleta, Lakewood, CO (US)

(73) Assignee: AI Arrive LLC, Lakewood, CO (US)

( * ) Notice: Subject to any disclaimer, the term of this patent is extended or adjusted under 35 U.S.C. 154(b) by 168 days.

(21) Appl. No.: 16/792,601

(22) Filed: Feb. 17, 2020

Related U.S. Application Data

(60) Provisional application No. 62/806,875, filed on Feb. 17, 2019.

(51) Int. Cl.
| | |
|---|---|
| *G06F 40/253* | (2020.01) |
| *G06F 40/205* | (2020.01) |
| *G16H 10/60* | (2018.01) |
| *G06K 9/62* | (2022.01) |
| *G06K 9/00* | (2022.01) |

(52) U.S. Cl.
CPC .......... *G06F 40/253* (2020.01); *G06F 40/205* (2020.01); *G06K 9/00456* (2013.01); *G06K 9/6262* (2013.01); *G16H 10/60* (2018.01)

(58) Field of Classification Search
CPC .................................................. G06F 40/253
See application file for complete search history.

(56) References Cited

U.S. PATENT DOCUMENTS

2007/0282590 A1* 12/2007 Suzuki et al. .......... G06F 17/28

* cited by examiner

*Primary Examiner* — James J Debrow

(57) ABSTRACT

Methods, systems, and apparatus, including computer programs language encoded on a computer storage medium for a logic sentence length reduction system whereby input text is modified to a logical and grammatical state using a reinforcement learning system with a real-time grammar engine and a real-time logic engine. The logic sentence length reduction system breaks sentences into fragments. An agent performs actions to each sentence fragment such that fragments are reconstructed into complete sentences. The real-time logic and real-time grammar engine are provided a reward for producing a grammatical and logical sentence. The reinforcement-learning agent optimizes a policy to reconstruct logical and grammatical sentences from sentence fragments maximizing future reward.

19 Claims, 12 Drawing Sheets

1) Negate Polar Words:
   Veins → -Arteries

2) Negate Antonym Pairs:
   Toward_heart(veins) → Away_heart(arteries)
   Away_heart(arteries) → Toward_heart(veins)

From_allPartsBody(veins) → -To_allPartsBody(arteries)
   To_allPartsBody(arteries) → -From_allPartsBody(veins)

3) Negate Relationships:
   blood_vessel(veins) → -blood_vessel(arteries)

1) Negate Polar Words:

Prepositional Logic:
   　　Veins → -Arteries
   FOL:

$\forall\ blood\_vessel(veins) \Rightarrow \neg\ \forall\ blood\_vessel(arteries)$

FIG. 9C

REINFORCEMENT LEARNING APPROACH TO DECODE SENTENCE AMBIGUITY

RELATED APPLICATIONS

This application claims priority to U.S. Provisional Patent Application No. 62/806,857 entitled "Reinforcement learning using a mental map to decode sentence ambiguity." Filed Feb. 17, 2019, the entirety of which is hereby incorporated by reference.

TECHNICAL FIELD

The present invention relates generally to Artificial Intelligence related to reinforcement learning for anaphora resolution and sentence ambiguity. In particular, the present invention is directed to natural language processing and reinforcement learning for decomposing sentences into sentence fragments and rebuilding sentence fragments into complete sentences that preserve anaphora integrity and the logical context of the original sentence. In particular, the present invention is directed to word relationship, network symmetry, formal logic, and reinforcement learning.

BACKGROUND

There are approximately 877,000 (AAMC The Physicians Foundation 2018 Physician Survey 2018) practicing doctors in the United States. The average number of patients seen per day in 2018 was 20.2 (Id. at pg. 22). The average amount of time doctors spend with patients has decreased to 20 minutes per patient (Christ G. et al. The doctor will see you now—but often not for long 2017). In this limited amount of time physicians are unable to properly explain complex medical conditions, medications, prognosis, diagnosis, and plans for self-care.

Patients' experience of healthcare in the form or written and oral communication is most often incomprehensible due to jargon filled language. Personalized information such as health records, genetics, insurance, etc. while most valuable and pertinent is completely inaccessible to most individuals.

The ability to simplify jargon into plain understandable language can have significant benefits for, e.g., patients. For example, in a medical application, layman language can save lives because a patient that understands their condition, their medication, their prognosis, or their diagnoses will be more likely to be compliant and/or identify medical errors.

Doctors notes are often written with run-on sentences that need to be simplified into separate complete simplified sentences. The challenge with splitting sentences into sentence fragments and then rebuilding those fragments into complete independent sentences comes from the inherent ambiguity in language. Anaphora resolution is the problem of resolving references to earlier or later items in the sentence. In order to rebuild logical, coherent sentences a solution must be able to resolve anaphora ambiguity.

Manually rewriting run-on sentences found in doctors notes into simpler sentences would be a substantial cost to develop for use, e.g., in the healthcare system when healthcare and insurance companies are cutting back. The cost of having doctors simplify EHRs would be unwieldy.

An estimate: 877,000 (total active doctors)×20.2 (patients seen per day)×7.5 (additional minutes for simplifying an EHR note)/1440 (minutes in a day)~92,268 additional 24-hr days for the medical workforce per day of seeing patients. The average overall physician salary is $299,000 a year or $143/hour (Kane L, Medscape Physician Compensation Report 2018). Simplifying EHR would result in an additional total cost per year for the entire healthcare system of $4.8 B.

The unmet need is to simplify medical language by reducing run-on sentences into shorter complete sentences. The unmet need would only be accomplished with a logical sentence length reduction system that consists of hardware devices (e.g. desktop, laptop, servers, tablet, mobile phones, etc.), storage devices (e.g. hard drive disk, floppy disk, compact disk (CD), secure digital card, solid state drive, cloud storage, etc.), delivery devices (paper, electronic display), a computer program or plurality of computer programs, and a processor or plurality of processors. A logical sentence length reduction system when executed on a processor (e.g. CPU, GPU) would be able to transform language into plain language such that the final output would be reviewed by an expert and delivered to end users through a delivery device (paper, electronic display).

There are no solutions in the prior art that could fulfill the unmet need of simplifying medical language by reducing run-on sentences into shorter complete sentences that retain the intended meaning. The prior art is limited by software programs that require human input and human decision points, supervised machine learning algorithms that require massive amounts ($10^9$-$10^{10}$) of human generated paired labeled training datasets, algorithms that are unable to consider the logical context when rebuilding sentence fragments into sentences.

SUMMARY

This specification describes a logical sentence length reduction system that includes a reinforcement learning system, a real-time grammar engine, and a real-time logic engine implemented as computer programs on one or more computers in one or more locations. The logical sentence length reduction system components include input data, computer hardware, computer software, and output data that can be viewed by a hardware display media or paper. A hardware display media may include a hardware display screen on a device (computer, tablet, mobile phone), projector, and other types of display media.

Generally, the system rebuilds sentence fragments into complete sentences using a reinforcement learning system such that an agent learns a policy to rebuild sentences that are logical and grammatical. An environment that is the input sentence, an agent, a state (e.g. word, character, or punctuation), an action (e.g. noun selection, verb selection, any part-of-speech selection, deletion, insertion, substitution, rearrangement, capitalization, or lowercasing), a reward (positive—grammatical and logical sentence, negative—non-grammatical sentence and/or illogical), and a function approximator are the components of a reinforcement learning system. The reinforcement learning system is coupled to both a real-time grammar engine and a real-time logic engine such that each edit (action) made by an agent to the sentence results in a positive reward if the sentence is grammatical and logical or a negative reward if the sentence is either non-grammatical or non-logical. To improve performance a reinforcement learning system is constrained such that edits performed by an agent are only performed in a specific location, the operational window, defined by the location of the original sentence break and the noun phrase and verb phrase relative to the sentence fragment.

In general, one or more innovative aspects may be embodied in an operation window. An operational window is used to constrain an agent to only perform actions at a location defined by the location of the original sentence break and the noun phrase and verb phrase of the sentence fragment. For an example, the sentence 'I shot the elephant in my pajamas.' broken into sentence fragments becomes 'I shot the elephant', 'in my pajamas.'. The operation window for the sentence fragment 'I shot the elephant' which has a noun and verb phrase would start after the last word in the sentence and proceed with operations to the right. Whereas the sentence fragment 'in my pajamas' which has no noun and no verb phrase would start before the first word in the sentence fragment and proceed with appending words until the sentence has a noun and verb phrase. A noun and/or verb phrase may come from the beginning, middle, and/or towards the end of the sentence depending on the relative length of the sentence.

A reinforcement learning agent is learning a policy to optimize total future reward such that actions performed result in a logical and grammatical sentence. A grammatical sentence is defined by the productions of grammar and the subset of part-of-speech tags for all word(s), character(s), numeral(s), and/or punctuation(s) that belong to the sentence. A logical sentence is defined by the execution of the logic of the sentence and hence the underlying mathematical representation of the sentence against the local contextual logic of a discourse of sentences within the neighborhood of the sentence as well as a global logic of a discourse that is representative of the semantics of the words within the sentence.

In general, one or more innovative aspects may be embodied in a generalizable reward mechanism, a real-time grammar engine. A real-time grammar engine when provided with an input sentence, data sources (e.g. grammar, training data), computer hardware including a memory and a processor(s), and a computer program or computer programs when executed by a processor, outputs one of two values that specifies whether a particular sentence is grammatical or non-grammatical.

A generalizable reward mechanism is able to correctly characterize and specify intrinsic properties of any newly encountered environment. The environment of the reinforcement learning system is a hypothesis sentence or sentence fragment. An intrinsic property of a sentence is grammaticality, such that a sentence is or is not well formed in accordance with the productive rules of the grammar of a language. The measure of well formed is such that a sentence complies with the formation rules of a logical system (e.g. grammar).

The intrinsic property of grammaticality is applicable to any newly encountered sentence. In addition, grammaticality is an optimal principal objective for the logical sentence length reduction system defined in this specification.

A grammar engine builder computer program when executed on a processor or processors builds all of the components to construct a real-time grammar engine for a particular input sentence such that the real-time grammar engine can be immediately executed ('real-time') on a processor or processors to determine whether or not the input sentence is grammatical.

The grammar engine builder computer program when executed on a processor or processors is provided with a grammar such that the grammar generates a production rule or a plurality of production rules, whereby the production rules describe all possible strings in a given formal language.

The grammar engine builder computer program takes the input sentence and calls another computer program, a part-of-speech classifier, which for every word, character, numeric, and/or punctuation the part-of-speech classifier outputs a part-of-speech tag. The grammar engine builder computer program creates a grammar production rule or plurality of grammar production rules by generating the grammar rules that define the part-of-speech tags from the input sentence. The grammar engine builder computer program creates an end-terminal node production rule or plurality of end-terminal node production rules by mapping the part-of-speech tags and the words, character, and/or punctuation in the input sentence to the production rules.

The grammar engine builder computer program is provided with a parser computer program whereby residing on a memory and executed by a processor or processors provide a procedural interpretation of the grammar with respect to the production rules of an input sentence. The parser computer program searches through the space of trees licensed by a grammar to find one that has the required sentence along its terminal branches. The parser computer program provides the output signal upon receiving the input sentence. The output signal provided by the parser in real-time when executed on a processor or processors indicates grammaticality.

The grammar engine builder computer program generates the real-time grammar engine computer program by receiving an input sentence and building a specific instance of grammar production rules that are specific to the part-of-speech tags of the input sentence. The grammar engine builder computer program stitches together the following components: 1) grammar production rule or plurality of grammar production rules, 2) end terminal node production rule or plurality of end terminal node production rules that map to the part-of-speech tags of the input sentence, 3) a grammar parser.

The real-time grammar engine receives the input sentence, and executes the essential components: grammar production rules that have been pre-built for the input sentence, a grammar, and a parser. The real-time grammar engine parses the input sentence and informs a reinforcement learning system that the edits or modifications made by an agent to a sentence result in either a grammatical or non-grammatical sentence.

In some implementations a grammar can be defined as a generative grammar, regular grammar, context free grammar, context-sensitive grammar, or a transformative grammar.

In general, one or more innovative aspects may be embodied in a logic engine such that a sentence can be evaluated at the local contextual level and at the global semantic level. An embodiment includes the following steps and substeps: 1) transforming an input sentence into executable form wherein 1.1) an input sentence is received; and 1.2) a set of symbolic equations are derived from the input sentence; 2) transforming a discourse of neighboring sentences into a set of logical equations wherein 2.1) a discourse of neighboring sentence is received; and 2.2) a set of logical equations are derived from the discourse of neighboring sentences; 3) transforming a discourse of global semantic relationships into a set of logical equations wherein 2.1) a discourse of peer-reviewed high quality sentences with semantic relationships to the input sentence are received; and 2.2) a set of logical equations are derived from the discourse of globally semantic sentences. After extraction, pre-processing, and derivation of the set of logical equations that describe the sentence level, local contextual level, and global semantic level an automated theorem prover is used to evaluate the sentence. The logic engine returns a positive reward to the agent if the symbolic equations describing the sentence are consistent at a local contextual level and at a global semantic level. Alternatively, the logic engine returns a negative reward to the agent if the symbolic equations describing the sentence are inconsistent at either a local contextual level or at a global semantic level.

The real-time logic engine transforms a discourse being either local and contextual or global semantic into a set of logical equations, categorizes the equations into assumptions and conclusions whereby the automated theorem prover using the assumptions infers a proof whereby the conclusion is logical or not. The real-time logic engine has the ability to transform a discourse into a set of assumptions and conclusion by executing the following instruction set on a processor: 1) a word network is constructed using the discourse and 'a priori' word groups, such that the word network is composed of node-edges defining word relationships; 2) 'word polarity' scores are computed to define nodes of symmetry; 3) a set of negation relationship are generated using the word network, antonyms, and word polarity scores; 4) a set of logical equations is generated using an automated theorem prover type, negated relationships, word network, and discourse.

In some aspects the discourse of sentences and groups are used to construct a network whereby a group A of words is used as the edges and a group B of words is used as the nodes such that group A and group B could be any possible groups of words, characters, punctuation, numerical, properties and/or attributes of the sentences or words.

In some aspects, the word polarity score is defined between two nodes in the network whereby the nodes have symmetrical relation with respect to each other such that the nodes share common connecting nodes and/or antonym nodes.

In some aspects, either the network, antonyms, and/or the polarity score are used to create negated relationships among nodes in the network. The symmetrical axes in a word network defines a set of nodes that are negated. Antonyms or commonly shared words with the symmetrical nodes are also used to create negated relationships.

In some aspects the negated relationships are formulated as a formal propositional logic whereby an automated propositional logic theorem prover evaluates the propositional logic equations and returns a positive reward if the discourse is logical and a negative reward if the discourse is nonsensical.

In some aspects the negated relationships are formulated as a formal first-order logic whereby an automated first-order logic theorem prover evaluates the first-order logic equations and returns a positive reward if the discourse is logical and a negative reward if the discourse is nonsensical.

In some aspects the negated relationships are formulated as a formal second-order logic whereby an automated second-order logic theorem prover evaluates the second-order logic equations and returns a positive reward if the discourse is logical and a negative reward if the discourse is nonsensical.

In some aspects the negated relationships are formulated as a formal higher-order logic whereby an automated higher-order logic theorem prover evaluates the higher-order logic equations and returns a positive reward if the discourse is logical and a negative reward if the discourse is nonsensical.

In some aspects a user may provide a set of logical equations that contain a specific formal logic to be used as assumptions in the real-time logic engine. In another embodiment a user may provide a set of logical equations that contain a specific formal logic to be used as the conclusion in the real-time logic engine. In another embodiment a user may provide the logical equations categorized into assumptions and conclusions.

Some of the advantages include a methodology that 1) allows sentences fragments to be rebuilt while ensuring the grammaticality and logical consistency of the original sentence 2) provides the ability to evaluate sentences to determine if they are grammatical or not; 3) provides the ability to evaluate sentences to determine if they are logical and consistent with neighboring sentences or not; 4) provides the ability to evaluate sentences to determine if they are logical and consistent with in a global semantic context or not;

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 9A, 9B, & 9C depicts an example of logical equations extracted from the word network.

Figure 1:
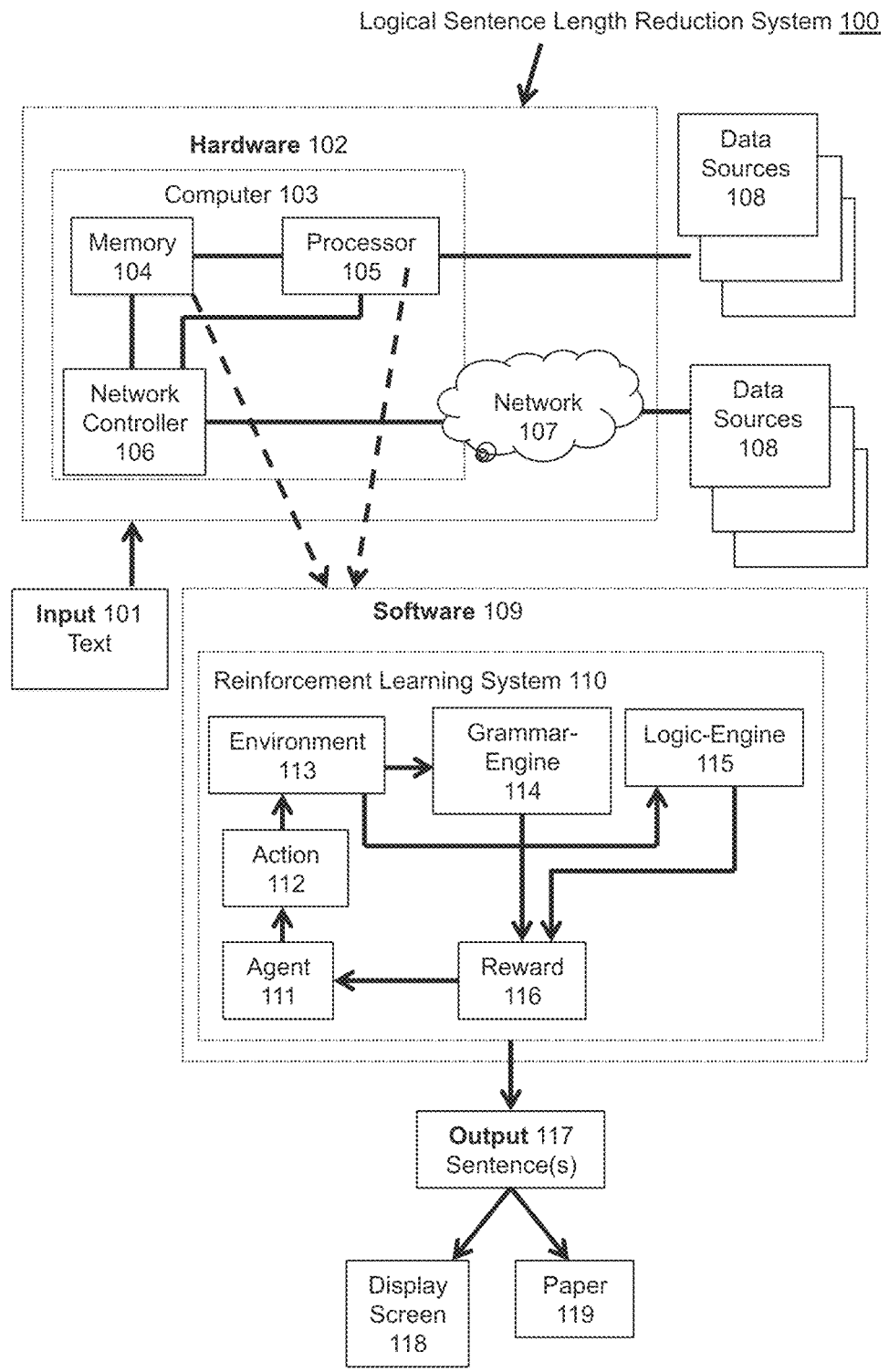
FIG. 1 illustrates a logical sentence length reduction system.

| DRAWINGS - REFERENCE NUMERALS | |
|---|---|
| 100 | Logical Sentence Length Reduction |
| 101 | Input Text System |
| 102 | Hardware |
| 103 | Computer |
| 104 | Memory |
| 105 | Processor |
| 106 | Network Controller |
| 107 | Network |
| 108 | Data Sources |
| 109 | Software |
| 110 | Reinforcement Learning System |
| 111 | Agent |
| 112 | Action |
| 113 | Environment |
| 114 | Grammar Engine |
| 115 | Logic Engine |
| 116 | Reward |
| 117 | Output sentence |
| 118 | Display Screen |
| 119 | Paper |
| 200 | Receive a sentence |
| 201 | Split a sentence |
| 202 | Hypothesis Sentences |
| 203 | Pool of states (sentence, action, reward) |
| 204 | Function Approximator |
| 300 | Grammar |
| 301 | Grammar Productions |
| 302 | POS classifier |
| 303 | POS tags |
| 304 | End terminal productions |
| 305 | Produce Computer Program |
| 306 | Execute Computer Program |
| 307 | Parse Sentence |
| 308 | Grammatical Reward |
| 400 | Discourse |
| 401 | Knowledge network |
| 402 | Word Network |
| 403 | Logical Language Mapper |
| 404 | Logical Equations |

-continued

DRAWINGS - REFERENCE NUMERALS

| | |
|---|---|
| 405 | Theorem Prover |
| 406 | Infer Proof |
| 407 | Logical Reward |
| 500 | Save Weights |
| 501 | Load Weights |
| 600 | Combined discourse |
| 601 | Extract Word Classes |
| 602 | Antonym Identification |
| 603 | Word Polarity Scores |
| 604 | Symmetry Extraction |
| 605 | Logical Relationships |
| 606 | Theorem Prover Type |
| 607 | Extract Semantics |
| 700 | Medical Word |
| 701 | Equivalence word |
| 702 | Noun Phrase |
| 800 | Polarity Scale |

DETAILED DESCRIPTION

Logical Sentence Length Reduction System

This specification describes a logical sentence length reduction system that includes a reinforcement learning system, a real-time logic engine, and a real-time grammar engine implemented as computer programs on one or more computers in one or more locations. The logic sentence length reduction system components include input data, computer hardware, computer software, and output data that can be viewed by a hardware display media or paper. A hardware display media may include a hardware display screen on a device (e.g. computer, tablet, mobile phone), projector, and other types of display media.

FIG. 1 illustrates a logic sentence length reduction system 100 with the following components: input 101, hardware 102, software 109, and output 117. The input is text such as a language in from a legal document, novel, electronic health record, a medical journal, and an insurance document, among others. The input 101 may be provided by an individual, individuals or a system and entered into a hardware device 102 such as a computer 103 with a memory 104, processor 105 and or network controller 106. A hardware device is able to access data sources 108 via internal storage or through the network controller 106, which connects to a network 107.

The data sources 108 that are retrieved by a hardware device 102 in one of other possible embodiments includes for example but not limited to: 1) an antonym and synonym database, 2) a thesaurus, 3) a corpus of co-occurrence words 4) a corpus of medical terms mapped to plain language definitions, 5) a corpus of medical abbreviations and corresponding medical terms, 6) a Formal logic grammar that incorporates all logical rules in a particular text input provided in any language, 7) a corpus of co-occurrence medical words, 8) a corpus of word-embeddings, 9) a corpus of part-of-speech tags, and 10) grammatical rules.

The data sources 108 and the text input 101 are stored in memory or a memory unit 104 and passed to a software 109 such as computer program or computer programs that executes the instruction set on a processor 105. The software 109 being a computer program executes a reinforcement learning system 110 on a processor 105 such that an agent 111 performs actions 112 on an environment 113, which calls a reinforcement learning reward mechanism, a grammar engine 114, and a logic engine 115, which provides a reward 116 to the system. The reinforcement learning system 110 reconstructs sentence fragments into complete sentences while ensuring that the intended meaning of the original sentence is preserved. The outputs 117 from the system are sentence(s) that may or may not have a shorter length than the original sentence extracted from the input text 101. The output 117 can be viewed by a reader on a display screen 118 or printed on paper 119.

In one or more embodiments of the logic sentence length reduction system 100 hardware 102 includes the computer 103 connected to the network 107. The computer 103 is configured with one or more processors 105, a memory or memory unit 104, and one or more network controllers 106. It can be understood that the components of the computer 103 are configured and connected in such a way as to be operational so that an operating system and application programs may reside in a memory or memory unit 104 and may be executed by the processor or processors 105 and data may be transmitted or received via the network controller 106 according to instructions executed by the processor or processor(s) 105. In one embodiment, a data source 108 may be connected directly to the computer 103 and accessible to the processor 105, for example in the case of an imaging sensor, telemetry sensor, or the like. In one embodiment, a data source 108 may be executed by the processor or processor(s) 105 and data may be transmitted or received via the network controller 106 according to instructions executed by the processor or processors 105. In one embodiment, a data source 108 may be connected to the reinforcement learning system 110 remotely via the network 107, for example in the case of media data obtained from the Internet. The configuration of the computer 103 may be that the one or more processors 105, memory 104, or network controllers 106 may physically reside on multiple physical components within the computer 103 or may be integrated into fewer physical components within the computer 103, without departing from the scope of the invention. In one embodiment, a plurality of computers 103 may be configured to execute some or all of the steps listed herein, such that the cumulative steps executed by the plurality of computers are in accordance with the invention.

A physical interface is provided for embodiments described in this specification and includes computer hardware and display hardware (e.g. computer screen). Those skilled in the art will appreciate that components described herein include computer hardware and/or executable software which is stored on a computer-readable medium for execution on appropriate computing hardware. The terms "computer-readable medium" or "machine readable medium" should be taken to include a single medium or multiple media that store one or more sets of instructions. The terms "computer-readable medium" or "machine readable medium" shall also be taken to include, but not be limited to, solid-state memories, and optical and magnetic media. For example, "computer-readable medium" or "machine readable medium" may include Compact Disc Read-Only Memory (CD-ROMs), Read-Only Memory (ROMs), Random Access Memory (RAM), and/or Erasable Programmable Read-Only Memory (EPROM). The terms "computer-readable medium" or "machine readable medium" shall also be taken to include any non-transitory storage medium that is capable of storing, encoding or carrying a set of instructions for execution by a machine and that cause a machine to perform any one or more of the methodologies described herein. In other embodiments, some of these operations might be performed by specific hardware components that contain hardwired logic. Those operations might alternatively be performed by any combination of programmable computer components and fixed hardware circuit components.

In one or more embodiments of the logic sentence length reduction system 100 software 109 includes the reinforcement learning system 110 which will be described in detail in the following sections.

In one or more embodiments of the logic sentence length reduction system 100 the output 117 includes language classified as follows: 1) logical language in which a sentence fragment is rebuilt to form a complete, grammatical, and logical sentence, 2) nonsensical sentence and/or a non-grammatical sentence that could not be resolved by the system. A user receiving the output sentences 117 through a hardware display screen 118 will have the option of saving the fixed content. A user can select this option through a hardware interface such as a keyboard, and/or cursor. The output sentences 117 will be delivered to an end user through a display screen 118 (e.g. tablet, mobile phone, computer screen) and/or paper 119.

Rebuilding Sentences within an Operation Window

The reinforcement learning system is constrained to perform operations on a sentence fragment within an operational window. The operational window is defined based on the location of the sentence break in the original sentence as well as the location of the noun phrase and/or verb phrase relative to the sentence break. As an example, the sentence 'I shot the elephant in my pajamas.' broken into sentence fragments becomes 'I shot the elephant', 'in my pajamas.'. The operation window for the sentence fragment 'I shot the elephant' which has a noun and verb phrase would start after the last word in the sentence fragment and proceed with operations to the right. Whereas, the sentence fragment 'in my pajamas' which has no noun and no verb phrase would start before the first word in the sentence fragment and proceed with appending words until the sentence has a noun and verb phrase.

The reinforcement learning system is tasked with identifying the correct noun phrase and verb phrase from the original sentence resulting in logical consistent and grammatically complete sentences. In order to reduce the search space and avoid nonsensical sentences an operational window defines the location at which words are to be appended to the sentence fragment. Constrained within the operation window the RL agent 111 performs an action 112 wherein a word, words, word phrases, numerical, character, and/or punctuation(s) are added to the operational window resulting in a new hypothesis sentence 202, which is passed along, to the grammar 114 and logic 115 engines resulting in a positive or negative reward. The grammar 114 and logic 115 engines provide the reward mechanism by which the agent can learn to optimize a policy to receive the maximal future rewards wherein the agent learns actions such as appending words that result in a grammatical and logical sentence.

Reinforcement Learning System

Further embodiments are directed to a reinforcement learning system that performs actions to a sentence or sentences whereby, a real-time grammar-engine reward mechanism returns a reward that is dependent on the grammaticality of the sentence and likewise, a real-time logic-engine reward mechanism returns a reward that is dependent on the logical validity of the sentence or sentences. The embodiment of a reinforcement learning system with a real-time grammar-engine and logic-engine reward mechanism enables actions such as reconstructing a sentence fragment into a logical, grammatical, and complete sentence.

Figure 2:
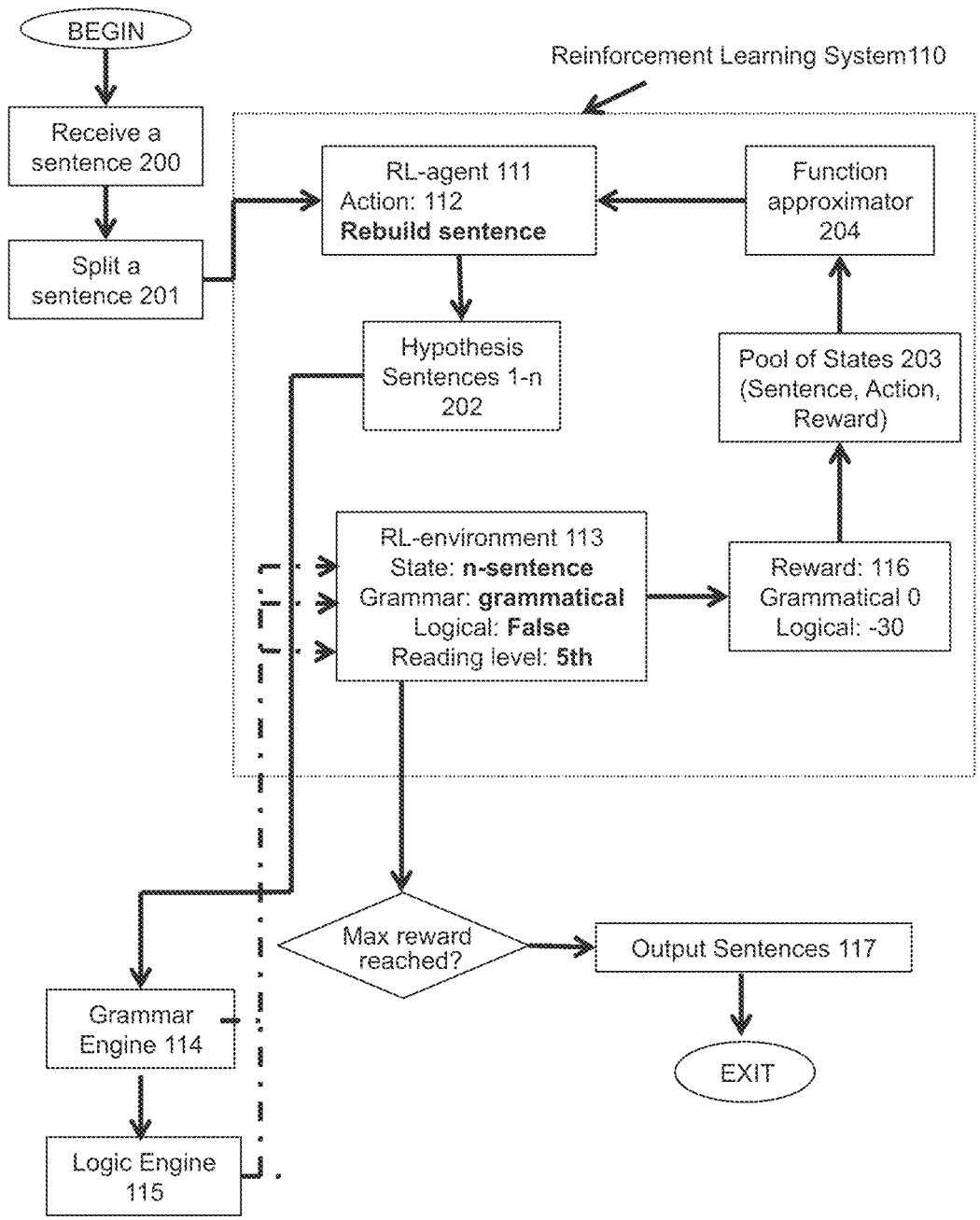
FIG. 2 depicts a reinforcement learning system.

A reinforcement learning system 110 with a grammar-engine and logic-engine reward mechanism is defined by an input 101, hardware 102, software 108, and output 117. FIG. 2. illustrates an example output to the reinforcement learning system 110 that may include but is not limited to shorter complete sentences that are constructed from the original sentence 200 that is extracted from the input text 101. Another input includes data sources 108 that are provide to the grammar engine 114 and logic engine 115 and function approximator 204 and will be described in the following sections.

The reinforcement learning system 110 uses a hardware 102, which consists of a memory or memory unit 104, and processor 105 such that software 109, a computer program or computer programs is executed on a processor 105 and performs edits to reconstruct the sentence fragment resulting in a logical and grammatical sentence or sentences. The output from reinforcement learning system 110 in an embodiment is combined in the same order as the original input text such that the original language is reconstructed to produce output language. A user is able to view the output sentences 117 on a display screen 118 or printed paper 119.

FIG. 2 depicts a reinforcement learning system 110 with a sentence(s) 200 that is split into sentence fragments 201 and an environment 113 that holds state information consisting of a sentence fragment or the reconstructed hypothesis sentence, and the grammatical and the logical validity of the sentence; such that an agent 111 performs actions 112 on a sentence; and a grammar engine 114 and a logic engine 115 are used as the reward mechanism returning a positive reward 116 if the sentence is grammatical and logical both in a local contextual and a global semantic scope. Whereas, a negative reward 116 will be returned if the sentence is either nonsensical and/or not grammatical. An agent receiving the sentence is able to perform actions 112 (e.g. noun selection, verb selection, any part-of-speech selection, deletion, insertion, substitution, rearrangement, capitalization, or lowercasing) on the sentence resulting in a new hypothesis sentence 202. The hypothesis sentence 202 is updated in the environment and then passed to a grammar engine 114 that updates the environment with a value that specifies the grammatical state (True-grammatical sentence, False-non-grammatical sentence) and similarly to a logic engine 115, which updates the environment with a value that specifies the logical state (True-logical sentence, False-non-logical sentence). Both the grammar engine 114 and the logic engine 115 return a reward 116 to the reinforcement-learning environment such that a change resulting in a logical and grammatical sentence results in a positive reward and a change resulting in a nonsensical sentence and/or a non-grammatical sentence results in a negative reward.

A pool of states 203 saves the state (e.g. hypothesis sentence), action (e.g. insertion), reward (e.g. positive). After exploration and generating a large pool of states 203 a function approximator 204 is used to predict an action that will result in the greatest total reward. The reinforcement learning system 110 is thus learning a policy to reconstruct sentence fragments resulting in grammatical and logically correct sentence(s). One or more embodiments specify termination once a maximum reward is reached and returns a set of grammatical and logically correct sentence(s). Additional embodiments may have alternative termination criteria such as termination upon executing a certain number of iterations among others. Also for given input sentence 200 it may not be possible to produce a grammatical and/or logical sentence 205 in such instances the original sentence could be returned and highlighted such that an end user could differentiate between simplified sentence and the original input text.

Figure 3:
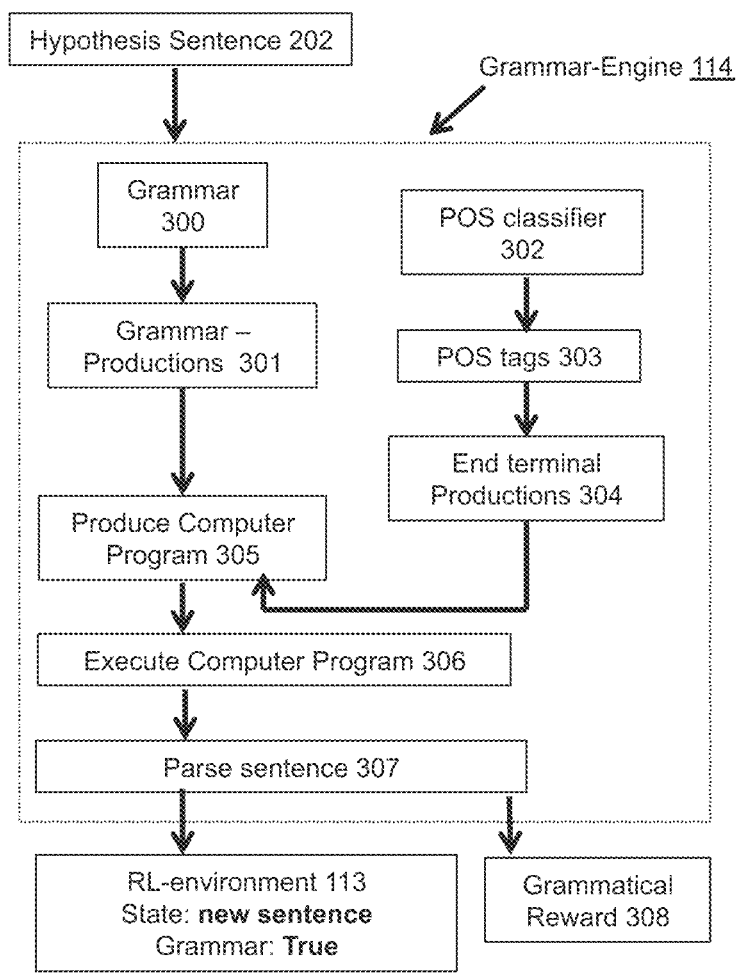
FIG. 3 depicts a grammar engine.

FIG. 3 illustrates the detailed components of the grammar engine 114. A grammar 300 is defined and used as an input data source 108 such that grammatical productions 301 are produced for the input sentence. A part-of-speech (POS) classifier 302 is used to determine the part-of-speech for each word, character, numerical, or punctuation in the sentence such that a POS tag 303 is returned. The POS tags 303 are then used to produce end terminal productions 304 for the corresponding grammar 300 that relates to the hypothesis sentence 200. The final grammar productions 301 and a parser are written to a computer program 305. The computer program stored in memory 104 receives the hypothesis sentence 202 and executes on a processor 105 such that the hypothesis sentence is parsed. The output of the grammar engine 114 is both an executable computer program 306 and the value 307 that specifies whether the sentence was grammatical or non-grammatical. A corresponding positive grammatical-reward 308 is given for a grammatical sentence and a negative grammatical-reward 309 is given for a non-grammatical sentence.

Figure 4:
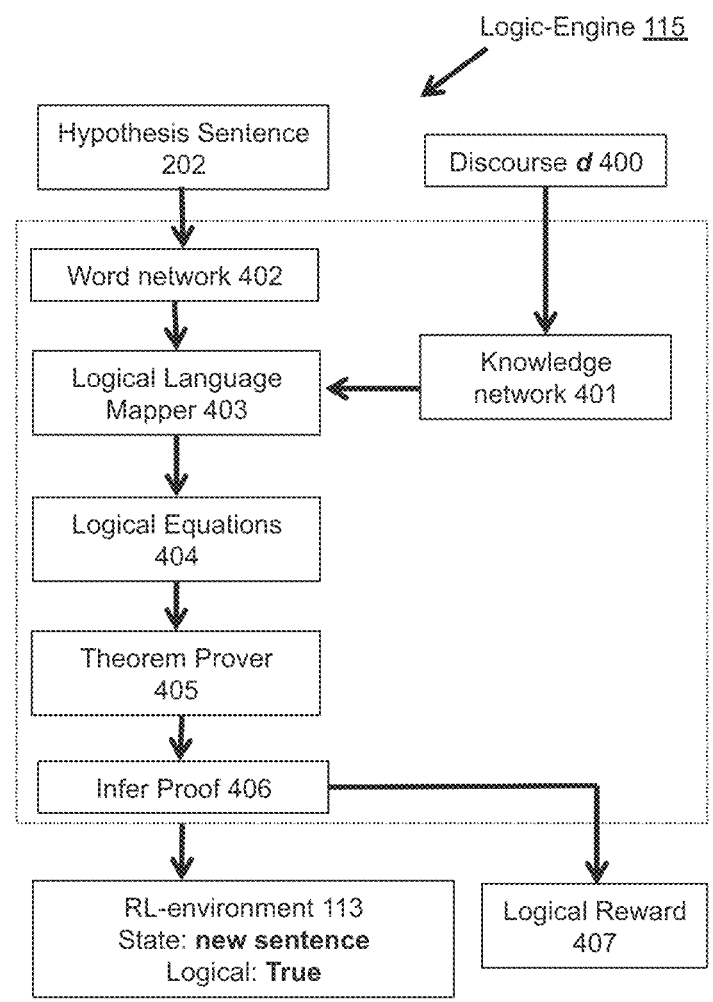
FIG. 4 depicts a logic engine.

FIG. 4 illustrates the detailed components of the logic engine 115. A hypothesis sentence 202 is configured into a word network 402 which will be described below in the sections to follow. A discourse 400, or a collection of sentence(s), paragraph(s), and/or document(s) is provided as a data source 108. There are two categories of discourses: 1) a local contextual discourse that comes from neighboring sentences within a paragraph, an entire paragraph, multiple paragraphs, or an entire text, and 2) a global semantic discourse which comes from a peer-reviewed literature, document, or any other text content filtered to only include sentences with words that overlap with the words of the hypothesis sentence 202. The discourse (e.g. local contextual or global semantic) is configured into a knowledge network 401.

The hypothesis sentence 202, discourse 400, word network 402 and knowledge networks 401 are provided as inputs to a logical language mapper function 403. The logical language mapper function 403 is used to formalize the networks into a formal language (e.g. first order logic) such that the output of logical equations 404 is compatible with the theorem prover 405. The theorem prover 405 residing in memory and executed on a processor 105 utilizes the logical equations 404 derived from the discourse 400 and the hypothesis sentence 202 as the premise and infers a proof 406. In essence, the theorem prover is validating that the stated assumptions (logical equations 404) logically guarantee the conclusion. The only way in which the stated assumptions logically guarantees the conclusion is if the logical equations are consistent and do not contradict one another, thus there must be consistency between the discourse 400 and the hypothesis sentence 202 being evaluated. The output of the logic engine 115 is a Boolean value that specifies whether the sentence was logical or not which is updated in the reinforcement-learning environment. A corresponding positive logical-reward 408 is given for compatibility between the hypothesis sentence 202 and the discourse 401 and a negative logical-reward 408 is given for incompatibility between the hypothesis sentence 202 and the discourse 401.

The reward 116 returned to the reinforcement learning agent 111 is positive if both the grammatical-reward 308 and logical-reward 407 are both positive and negative if either the grammatical-reward 308 and/or the logical-reward 407 are negative.

Figure 5:
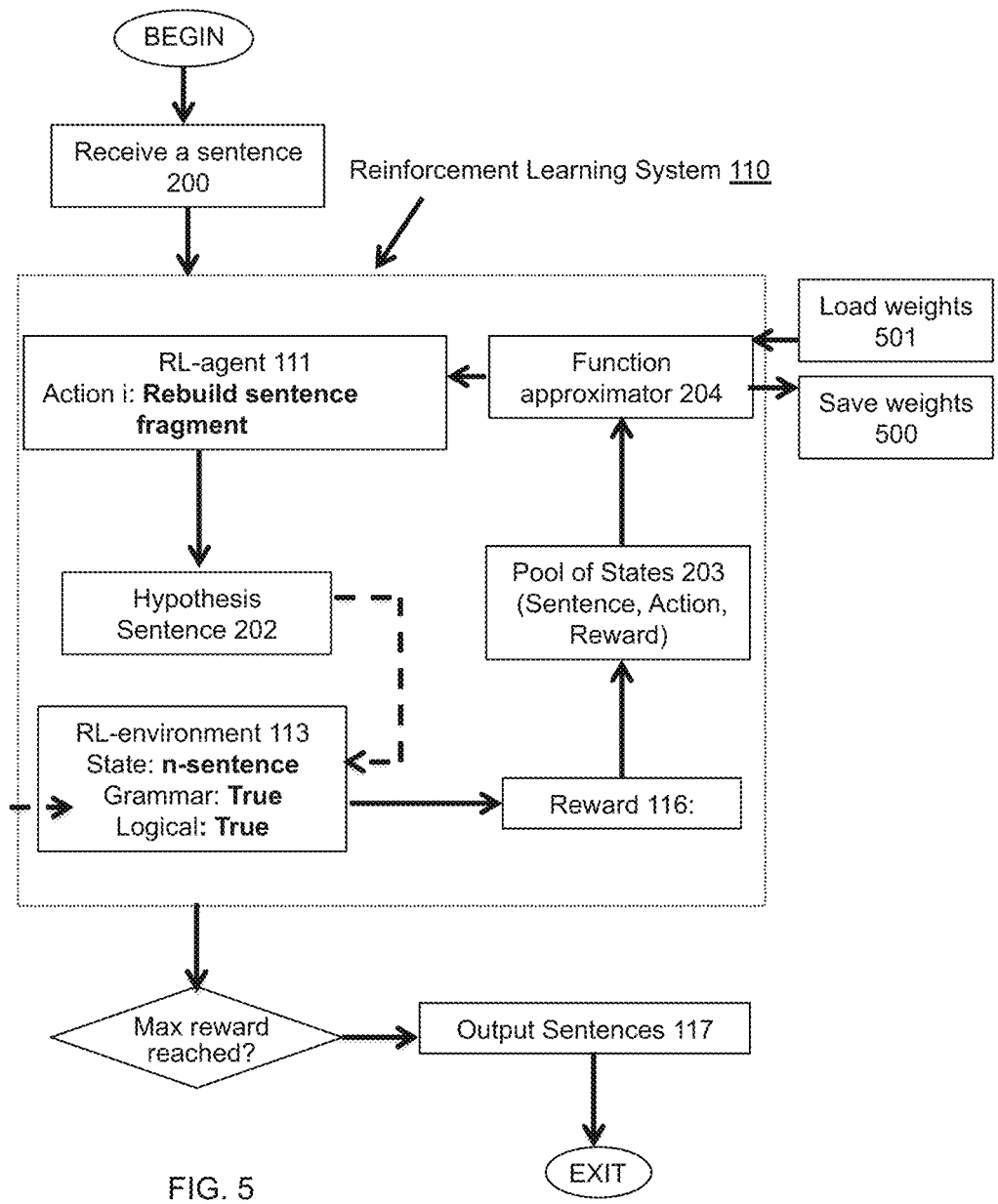
FIG. 5 depicts transfer learning.

FIG. 5 illustrates a reinforcement learning system 110 with a transferrable learning mechanism. The transferrable learning mechanism being weights from a function approximator 204 (e.g. convolutional neural network CNN) that has optimized a learning policy whereby edits that result in a complete grammatical and logical sentence has been learned. The weights from a function approximator can be stored in a memory 104 such that the weights are saved 500. The weights can be retrieved 501 by a reinforcement learning system 110 and loaded into a function approximator 204. The transferrable learning mechanism enables the optimal policy from a reinforcement learning system 110 to be transferred to a naive reinforcement learning system 110 such that the system 110 will have a reduction in the amount of time required to learn the optimized policy.

Real-Time Grammar Engine

One or more aspects includes a real-time grammar engine, which consists of a shallow parser and a grammar, such as, but not limited to, a context free grammar, which is used to evaluate the grammar of the sentence and return a reward or a penalty to the agent. A real-time grammar engine is defined by an input (101, 202), hardware 102, software 108, and output (113 & 308). A real-time grammar engine at operation is defined with a hypothesis sentence 202 that has been modified by a reinforcement learning system 110, a software 109 or computer program that is executed on hardware 102 that includes a memory 104 and a processor 105 resulting in an output a value that specifies a grammatical sentence vs. a non-grammatical sentence. The output value updates the reinforcement learning system environment (113) and provides a grammar-reward (308) such that together with a logic-reward 407, a total reward 116 is returned to the agent (111).

One or more aspects of a context free grammar, as defined in formal language theory, is a certain type of formal grammar such that sets of production rules describe all possible strings in a given formal language. These rules can be applied regardless of context. A formal language theory deals with the hierarchies of language families defined in a wide variety of ways and is purely concerned with the syntactical aspects rather than the semantics of words. They can also be applied in reverse to check whether a string is grammatically correct. These rules may include all grammatical rules that are specified in any given language.

One or more aspects of a parser processes input sentences according to the productions of a grammar, and builds one or more constituent structures that conform to the grammar. A parser is a procedural interpretation of the grammar. The grammar is a declarative specification of well-formedness such that when a parser evaluates a sentence against a grammar it searches through the space of trees licensed by a grammar to find one that has the required sentence along its terminal branches. If a parser fails to return a match the sentence is deemed non-grammatical and if a parser returns a match the sentence is said to be grammatical.

An advantage of a grammar engine is that it has sustained performance in new environments. An example is that the grammar engine can correct a sentence from doctor's notes and another sentence from a legal contract. The reason being that grammar engine rewards an agent based on whether or not a sentence parses. The grammaticality of the sentence is a general property of either a sentence from a doctor's note or a sentence in a legal contract. In essence in selecting a reward function, the limited constraint introduced in the aspect of the reinforcement learning grammar-engine was the design decision of selecting a reward function whose properties are general to new environments.

A reinforcement learning system updates a policy such that modifications made to a sentence are optimized to a grammatical search space. A grammatical search space is generalizable and scalable to any unknown sentence that a reinforcement learning system may encounter.

A real-time grammar engine in operation, which receives a sentence 202, and then outputs a computer program with grammar rules that when executed on a processor 105 return the grammaticality of the hypothesis sentence 202. First the hypothesis sentence 202 is parsed to generate a set of grammar rules. A parse tree is generated from the sentence; the sentence is received 202 from the reinforcement learning environment 113; each word in the sentence is tagged with a part-of-speech tag 303; a grammar rule with the start key S that defines a noun, verb, and punctuation is defined 301; a shallow parser grammar is defined, such as a grammar that chunks everything as noun phrases except for verbs and prepositional phrases; the shallow parser grammar is evaluated using a parser, such as nltk.RegexpParser; and parse the part-of-speech tagged sentence using the shallow parser.

After parsing the sentence a set of grammar rules are loaded into memory. The grammar rules start with the first rule that includes the start key S that defines a noun, verb, and punctuation; a grammar rule is initialized for each part-of-speech tag in the sentence; then for each segment in the parse tree a production is appended to the value corresponding part-of-speech keys for the grammar rules; additional atomic features for each individual grammar tags, such as singularity and plurality of nouns, are added to the grammar rules; all intermediate production are produced, such as PP→IN NP; finally, for each word in the sentence a production is created which corresponds to the words POS tag and appends a new grammar rule (e.g. NNS→dogs).

After creating a set of grammar rules and productions the grammar rules are written to a computer program stored on a memory 104, which is then used to evaluate the grammaticality of the sentence by executing the computer program on a processor 105. The computer program is executed on a processor 105; and if the sentence parses return value True otherwise value False. The value is returned to the reinforcement learning system 110 such that a positive grammatical-reward 308 is returned if the sentence parse returns a True and a negative grammatical reward 308 is returned if the sentence parse returns False.

In some implementations a grammar, a set of structural rules governing the composition of clauses, phrases, and words in a natural language maybe defined as a generative grammar whereby the grammar is a system of rules that generates exactly those combinations of words that form grammatical sentences in a given language. A type of generative grammar, a context free grammar, specifies a set of production rules describe all possible strings in a given formal language. Production rules are simple replacements and all production rules are one-to-one, one-to-many, or one-to-none. These rules are applied regardless of context.

In some implementations a grammar maybe defined as a regular grammar whereby a formal grammar is right-regular or left-regular. A regular grammar has a direct one-to-one correspondence between the rules of a strictly right regular grammar and those of a nondeterministic finite automaton, such that the grammar generates exactly the language the automaton accepts. All regular grammars generate exactly all regular languages.

In some implementations a grammar maybe defined as a context-sensitive grammar such that the syntax of natural language where it is often the case that a word may or may not be appropriate in a certain place depending on the context. In a context-sensitive grammar the left-hand sides and right-hand sides of any production rules may be surrounded by a context of terminal and nonterminal symbols.

In some implementations a grammar maybe defined as a transformative grammar (e.g. grammar transformations) such that a system of language analysis recognizes the relationship among the various elements of a sentence and among the possible sentences of a language and uses processes or rules called transformations to express these relationships. The concept of transformative grammars is based on considering each sentence in a language as having two levels of representation: a deep structure and a surface structure. The deep structure is the core semantic relations of a sentence and is an abstract representation that identified the ways a sentence can be analyzed and interpreted. The surface structure is the outward sentence. Transformative grammars involve two types of production rules: 1) phrase structure rules 2) transformational rules such rules that convert statements to questions or active to passive voice, which acted on the phrase markers to produce other grammatically correct sentences.

Real-Time Logic Engine

One or more aspects includes a real-time logic engine, which consists of a logical language mapper that transforms the hypothesis sentence 202 and discourse 400 into a set of logical equations 404 that are evaluated in real-time using the automated theorem prover 405. A real-time logic engine is defined by an input 202, hardware 102, software 114, and output (113 & 407). A real-time logic engine at operation is defined with the following components: 1) hypothesis sentence 202 and input discourse 400; 2) a software 109 or computer program; 3) hardware 102 that includes a memory 104 and a processor 105 4) an output a value 308 that specifies a logical or nonsensical sentence. The output value updates the reinforcement learning system environment 113 and provides a logical-reward 407 used in part to determine the overall reward 116 that is returned to the agent 111.

One or more aspects of the logical equations, as defined in formal language theory, is a certain type of formal logic such that premises or assumptions are used to infer a conclusion. These logical equations can be derived regardless of content. Mathematical logic derives from mathematical concepts expressed using formal logical systems. The systems of propositional logic and first order logic (FOL) are less expressive but are desirable for proof theoretic properties. Second order logic (SOL) and higher order logic (HOL) are more expressive but are more difficult to infer proofs.

Logical Language Mapper

The combined discourse 600 with a set of a finite number of sentences is transformed into a set of logical equations such that the logical equations are compatible as evaluated by the automated theorem prover. The following steps are executed by a processor with a software and input data residing in memory: 1) sentences are transformed into a network of word relationships; 2) antonyms are identified in the network; 3) word polarity score is calculated for each node with respect to all neighboring nodes; 4) using polar word scores, antonyms, and the symmetry of the word network equations are generated that reflect the symmetry of word relationships in the network; 5) input theorem prover type informs the logical language mapper such that semantics are extracted from the original sentences and used to output the appropriate logical form for the equations.

Figure 6:
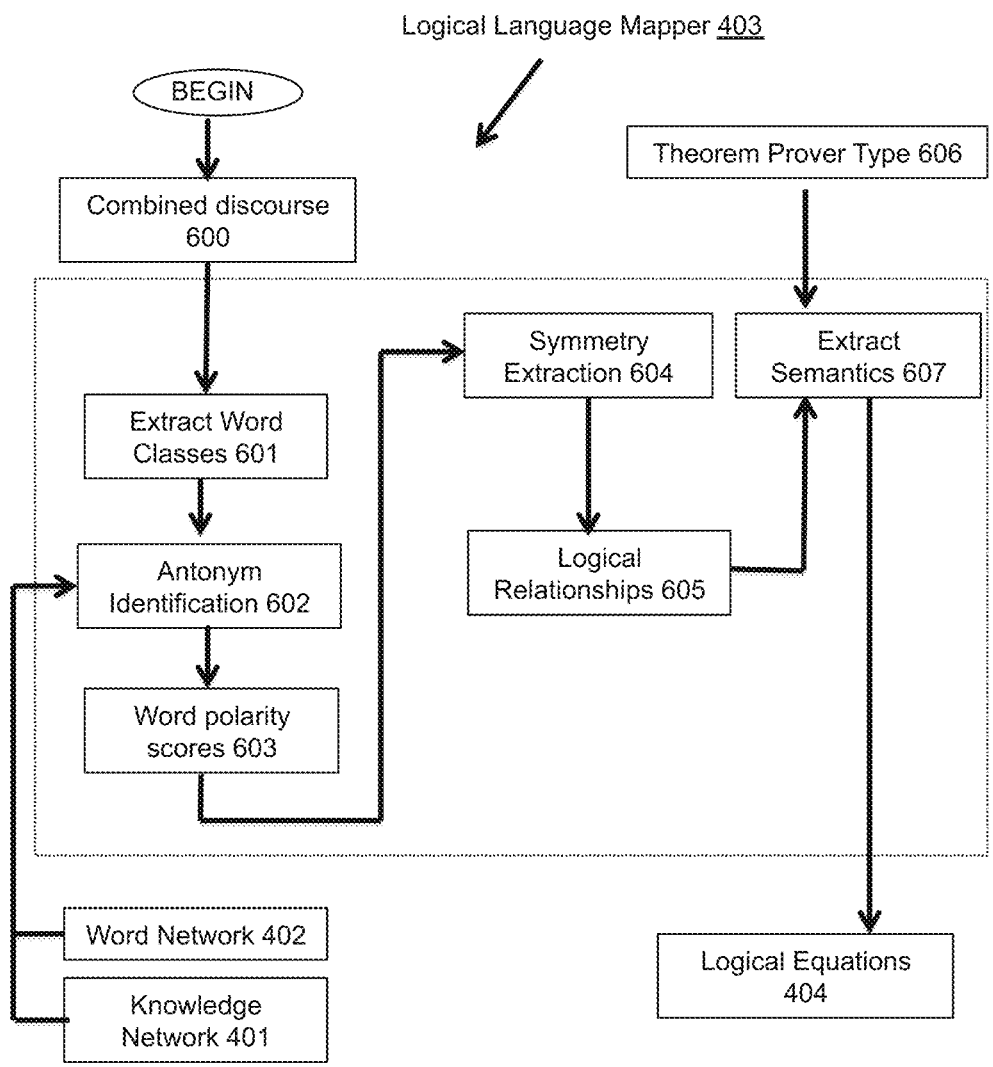
FIG. 6 depicts a logic language mapper.

FIG. 6 illustrates the logical language mapper 403 which takes as input the combined discourse 600, word network 402, and the knowledge network 401 residing in memory. A computer program or computer program(s) residing in memory and executed as an instruction set on a processor 105 transforms the combined discourse 600 into a set of logical equations 404 residing in memory. FIG. 6 shows the following steps executed as an instruction set on a processor 105: 1) extract word classes 601; 2) identify antonyms 602; 3) compute word polarity scores 603, for each node with respect to all neighboring nodes; 4) use symmetry of the network to extract negation relationships 604 in the word network 402 and knowledge network(s) 403; 5) use as input theorem prover type 606 as an argument residing in memory such that the computer program or computer programs residing in memory and executed as an instruction set on a processor 105 extract the semantics from the word network 402, knowledge network 403, and/or the combined discourse 600 and use the extracted semantics 607 to generate a set of logical equations 404 that are compatible with the automated theorem prover 405.

Word Network

The word network 402 is a graphical representation of the relationships between words represented as nodes and relationship between words are edges. Nodes and edges can be used to represent any or a combination of parts-of-speech tags in a sentence or word groups within the sentence defined as word classes. An embodiment of a word network may include extracting the subject and object, from a sentence such that the subject and object are the nodes in the network and the verb or adjective is represented as the edge of the network. Another embodiment may extract verbs as the nodes and subjects and/or objects as the edges. Additional combination of words and a priori categorization of word relationships defined as word classes are within the scope of this specification for constructing a word network 402.

The following steps provide an example of how a word network could be constructed for a Wikipedia medical page such that an input of the first five sentences of Wikipedia medical page is provided to the system and an output of the medical word network 402 is produced from the system. The first step, the combined discourse 600 is defined as Wikipedia medical page and the first five sentences are extracted from the input corpus. The second step, a list of English equivalency words is defined. In this embodiment the English equivalency words are the following 'is', 'are', 'also referred as', 'better known as', 'also called', 'another name' and 'also known as' among others. The third step, filter the extracted sentences to a list of sentences that contain an English equivalency word or word phrase. The fourth step, apply a part-of-speech classifier to each sentence in the filtered list. The fifth step, group noun phrases together. The sixth step, identify and label each word as a subject, objective, or null. The seventh step, create a mapping of subject, verb, object to preserve the relationship. The eighth step, remove any words in the sentence that are not a noun or adjective, creating a filtered list of tuples (subject, object) and a corresponding mapped ID. The ninth step, identify and label whether or not a word in the tuple (subject, object) exist in the network. The tenth step, for tuples that do not exist in the network add a node for the subject and object, the mapped ID for the edge, and append to the word network 402. The eleventh step, for tuples that contain one word that does exist in the network, add the mapped ID for the edge, and the remaining word that does not exist in the word network as a connecting node. The twelfth step, for tuples that exist in the network pull the edge with a list of mapped IDs if the mapped ID corresponding to the tuple does not exist append the mapped ID to the list of mapped IDs that correspond with the edge otherwise continue.

Figure 7A:
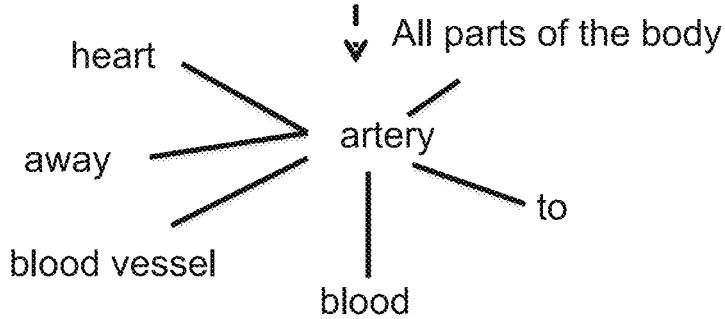
FIGS. 7A & 7B depicts deriving a word network from a sentence.
Figure 7B:
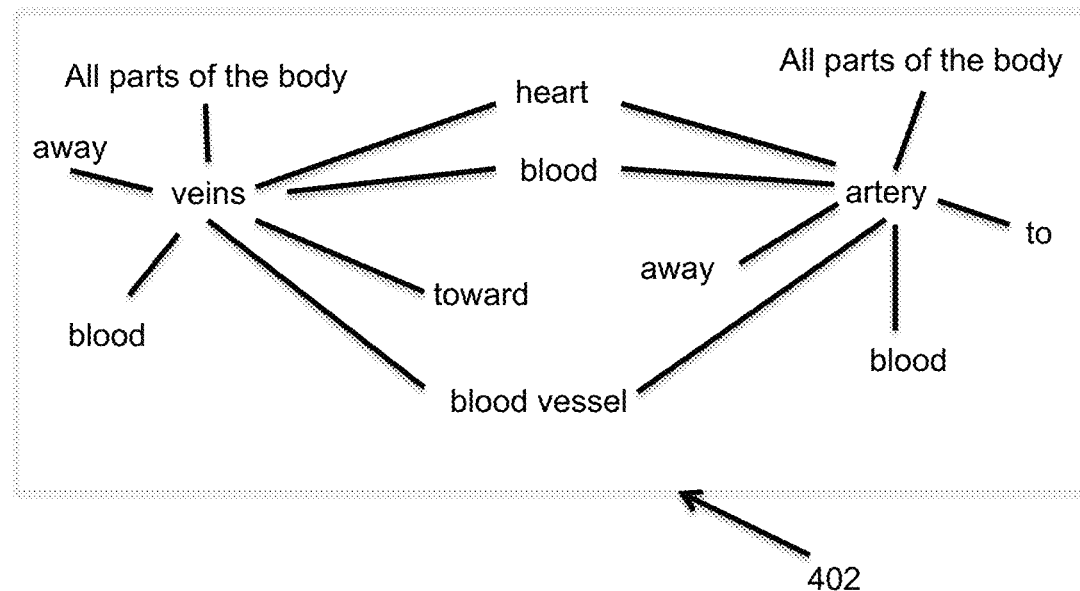

FIGS. 7A & 7B shows how a medical sentence is turned into a word network 402. A medical word 700 is extracted by first identifying an English equivalence word 701, which in this example is the word 'is'. Noun phrases 702 within the sentence are grouped together. Then the medical word 700 is equated to the words on the right side of the equivalence word. All words that are not noun or adjective are removed from the sentences except for words that are part of the grouped noun phrases 702. A word network 402 is constructed for the word 'artery'. The same process is repeated for the word 'veins'. The final word network 402 that connects nodes between the medical words 700 'veins' and 'arteries' is shown in FIG. 7B.

Word Polarity

A word polarity system performs step 603 with the following components: input 101, hardware 102, software 109, and output 603. The word polarity method requires an input word network 402, or knowledge network 401 and antonym identification 602, hardware 102 consisting of a memory 104 and a processor 105, software 109 (word polarity computer program) and output word polarity scores 603 residing in memory. The word polarity system can be configured with user specified data sources 108 to return nodes in the word network 402 that are above a word polarity threshold score. The word polarity identification system can be configured with user specified data sources 108 to use an ensemble of word polarity scoring methods or a specific word polarity scoring method.

Figure 8:
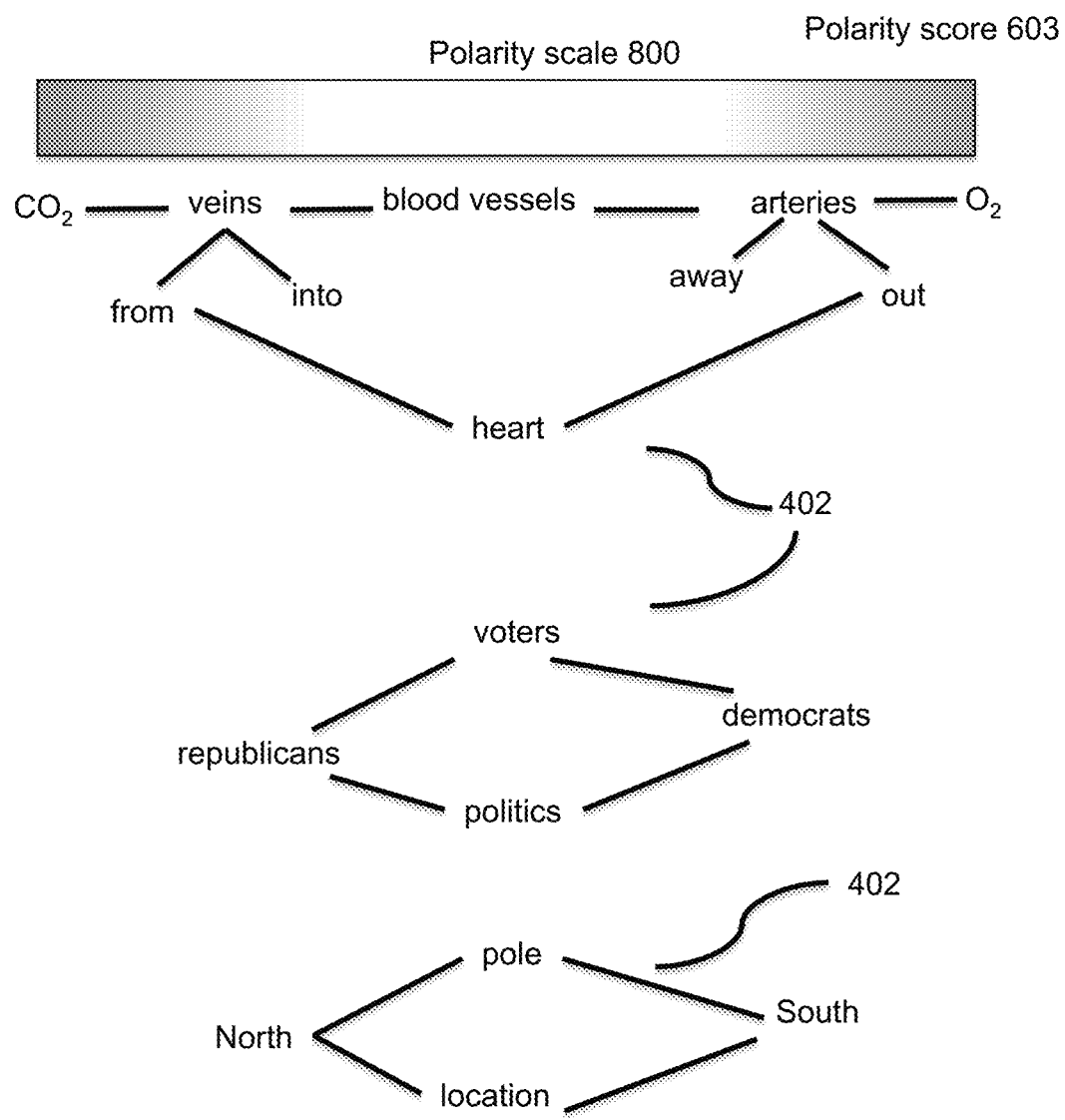
FIG. 8 depicts word polarity from word networks.

FIG. 8 shows three examples of 'polar' words that can be identified from the word network 402. In this first network the words with the highest polarity scores 603, as defined by the polarity scale 800 are the words 'veins' and 'arteries'. The words 'veins' and 'arteries' are symmetrical indicating that they are polar opposites. Arteries being defined as 'blood vessels that carry oxygenated blood (O2) away from the heart' which is symmetrical in meaning with veins, defined as 'blood vessels that carry deoxygenated blood to the heart'. The word 'arteries' and 'veins' are symmetrical in other aspects consider these definitions: 'Arteries bring oxygen rich blood to all other parts of the body.' and 'Veins carry carbon dioxide rich blood away from the rest of the body.' Polar words have reference words in common for the example of 'arteries' and 'veins' the shared reference words are 'blood vessels' and 'heart'. They also have antonym words shared between them such as 'carry out' (arteries) and 'carry into' (veins), 'oxygenated blood $O_2$ (arteries)' and 'deoxygenated blood $CO_2$ (veins)', and 'carry blood to the body (arteries)' and 'carry blood away from the body (veins)'.

Similar words that are symmetrical include 'Republicans' and 'Democrats', 'North' and 'South' (FIG. 8) The reference words for 'Republicans' and 'Democrats' are 'voters', 'politics', 'convention', 'primary', etc. among others and reference words for 'North' and 'South are 'pole', 'location', 'map' etc. Symmetrical words are similar in size in terms of the number of nodes that they are connected to.

Neutral words with low word polarity scores are words such as 'blood vessels', 'heart', and 'location'. The word 'heart' in relation to medicine has no 'polar word' that has opposite and relating functions and attributes. However, outside of medicine in literature for example the word 'heart' may have a different polarity score perhaps 'heart' relates to 'love' vs. 'hate'. The polarity scores of words can change depending on their underlying corpus.

In some implementations the word polarity computer program, computes a word polarity score 603 for each node in relation to another node in the word network 402. The polarity score 603 is calculated based on shared reference nodes $N_{ref}$ and shared antonym nodes $N_{An}$. The node polarity connections are defined as $N_{polarity}=w_s N_{Ref}+w_A N_{Ant}$. A global maximum polarity score is $Max_{polarity}=Max(N_{polarity})$ is computed across the word network 402. The word polarity score 603 is computed as $P_{score}=N_{polarity}/Max_{polarity}$ with respect to each node $N_i$ interacting with node $N_j$.

In some implementations the word polarity computer program, computes a word polarity score 603 by identifying the axis with the largest number of symmetrical nodes within the word network 402. The summation of nodes along the axis that maximizes symmetry defines a node polarity connection score $N_{polarity}=\Sigma_{i,j \in S_k} n_{ij}$ such that i, j represent nodes in relation to each other in the subnetwork $S_k$ computed for all nodes in the word network 402. A global maximum polarity score is $MaX_{polarity}=max(N_{polarity})$ is computed across the word network 402. The word polarity score 603 is computed as $P_{score}=N_{polarity}/Max_{polarity}$ with respect to each node $N_i$ interacting with node $N_j$.

Symmetry Extraction

A symmetry extraction method performs step 604 with the following components: input 101, hardware 102, software 109, and output 605. The symmetry extraction method requires an input word network 402, and antonym identification 602, hardware 102 consisting of a memory 104 and a processor 105, a software 109 and output logical relationships 605 residing in memory. The symmetry extraction can be configured with user specified data sources 108, theorem prover type 606 to return logical equations 404 with the following steps: 1) symmetry is used to generate negations between polar words in the word network resulting in negated logical relationships 2) using the input of a theorem prover type 606 extract semantics 607 to formalize the logical relationships 605 into a formal logic (e.g. FOL) resulting in the output of logical equations 404.

Figure 9A:
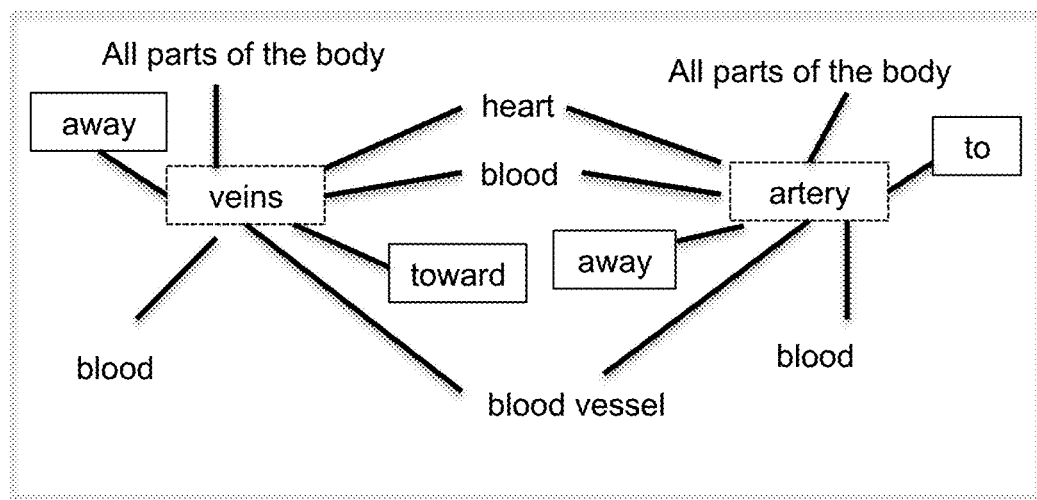
Figure 9B:
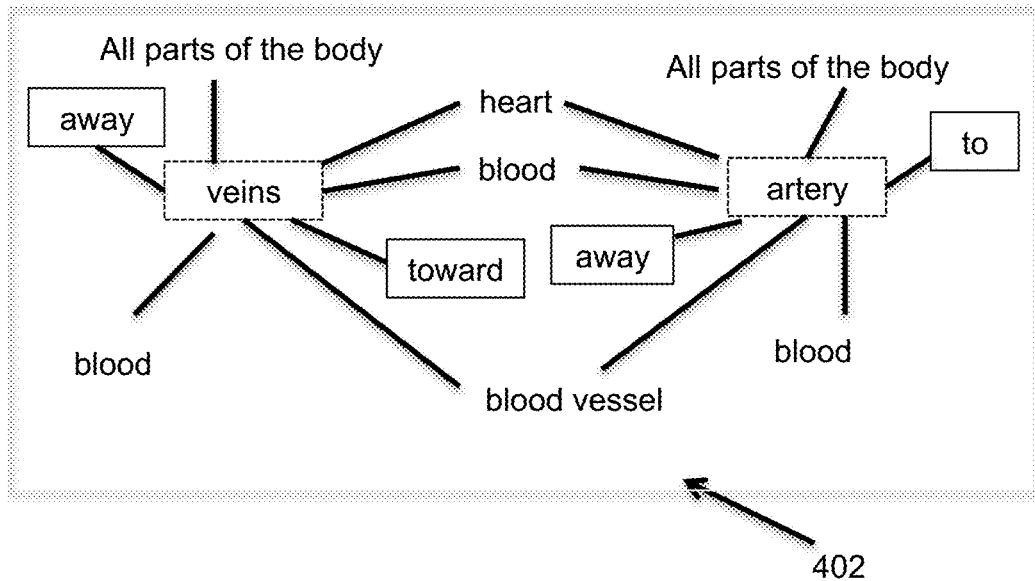

FIGS. 9A, 9B, & 9C illustrates the steps for generating logical relationships 605 that are then formulated into logical equations 404 using as input the word polarity scores 603, word network 402, and antonyms 602. FIG. 9A shows a word network 402 in which the nodes in the top list of word polarity scores 900 is shown in the dashed boxes and the antonyms 901 are shown in the solid boxes. The steps for generating logical relationships 605 from the word network 402 are shown in FIG. 9B. The steps are the following: 1) negate polar words, 2) negate antonym pairs, 3) negate relationships. FIG. 9C shows an example of extracting semantics from the sentences of the combined discourse 600 and/or word network 402 in a formal language and thus generating logical equations 405.

FIG. 9C shows the example of negating the polar words and outputting propositional logic and FOL. It should be noted that someone skilled in the art is able to transform English sentences into a formal language of logic. The symmetry extraction method transforms the English sentences into a formal language of logic as shown in FIG. 9C whereby a set of rules maps English sentences into formal languages. It should be noted that it maybe impossible to transform some sentences and word network relationships into types of logic (e.g. HOL) and/or any logical form. If it is not possible to transform some sentences into a logical form the following steps will be performed: 1) automatically changing the automated theorem prover and deriving the set of logical equations for that theorem prover until all options are exhausted; 2) returning an error and/or logging the error.

Theorem Prover

In some implementations a theorem prover computer program, evaluates symbolic logic using an automated theorem prover derived from first-order and equational logic. Prover9 is an example of a first-order and equational logic automated theorem prover (W. McCune, "Prover9 and Mace4", http://www.cs.unm.edu/~mccune/Prover9, 2005-2010).

In some implementations a theorem prover computer program, evaluates symbolic logic using a resolution based theorem prover. The Bliksem prover, a resolution based theorem prover, optimizes subsumption algorithms and indexing techniques. The Bliksem prover provides many different transformations to clausal normal form and resolution decision procedures (Hans de Nivelle. A resolution decision procedure for the guarded fragment. Proceedings of the $15^{th}$ Conference on Automated Deduction, number 1421 in LNAI, Lindau, Germany, 1998).

In some implementations a theorem prover computer program, evaluates symbolic logic using a first-order logic (FOL) with equality. The following are examples of a first-order logic theorem prover: SPAS S (Weidenbach, C; Dimova, D; Fietzke, A; Kumar, R; Suda, M; Wischnewski, P 2009, "SPASS Version 3.5", CADE-22: 22nd International Conference on Automated Deduction, Springer, pp. 140-145), E theorem prover (Schulz, Stephan (2002). "E-A Brainiac Theorem Prover" Journal of AI Communications. 15 (2/3): 111-126), leanCoP In some implementations a theorem prover computer program, evaluates symbolic logic using an analytic tableau method. LangPro is an example analytic tableau method designed for natural logic. LangPro derives the logical forms from syntactic trees, such as Combinatory Categorical Grammar derivation trees. (Abzianidze L., LANGPRO: Natural Language Theorem Prover 2017 In Proceedings of the 2017 Conference on Empirical Methods in Natural Language Processing: System Demonstrations, pages 115-120).

In some implementations a theorem prover computer program, evaluates symbolic logic using an reinforcement learning based approach. The Bare Prover optimizes a reinforcement learning agent over previous proof attempts (Kaliszyk C., Urban J., Michalewski H., and Olsak M. Reinforcement learning of theorem proving. arXiv preprint arXiv:1805.07563, 2018). The Learned Prover uses efficient heuristics for automated reasoning using reinforcement learning (Gil Lederman, Markus N Rabe, and Sanjit A Seshia. Learning heuristics for automated reasoning through deep reinforcement learning. arXiv:1807.08058, 2018.) The $\pi_4$ Prover is a deep reinforcement learning algorithm for automated theorem proving in intuitionistic propositional logic (Kusumoto M, Yahata K, and Sakai M. Automated theorem proving in intuitionistic propositional logic by deep reinforcement learning. arXiv preprint arXiv:1811.00796, 2018.)

In some implementations a theorem prover computer program, evaluates symbolic logic using higher order logic. The Holophrasm is an example automated theorem proving in higher order logic that utilizes deep learning and eschewing hand-constructed features. Holophrasm exploits the formalism of the Metamath language and explores partial proof trees using a neural-network-augmented bandit algorithm and a sequence-to-sequence model for action enumeration (Whalen D. Holophrasm: a neural automated theorem prover for higher-order logic. arXiv preprint arXiv:1608.02644, 2016.)

Operation of Reinforcement Learning System

One of the embodiments provides a grammar engine and a logic engine such that a sentence can be evaluated in real-time and a set of actions performed on a sentence that does not parse or is incompatible with prior knowledge in order to restore the grammatical structure and logical validity to the sentence. In this embodiment a sentence and thus its attributes (e.g. grammar, logical) represents the environment. An agent can interact with a sentence and receive a reward such that the environment and agent represent a Markov Decision Process (MDP). The MDP is a discrete time stochastic process such that at each time step the MDP represents some state s, (e.g. sentence fragment, and or hypothesis sentence) and the agent may choose any action a that is available in state s. The process responds at the next time step by randomly appending words to the sentence fragment resulting in a new state s'2 and passing new state s'2 residing in memory to a real-time grammar engine and real-time logic engine that when executed on a processor returns a corresponding reward $R_a$ (s,s2) for s'2.

The benefits of this and other embodiments include the ability to evaluate and correct a sentence in real-time. This embodiment has application in many areas of natural language processing in which a sentence fragments maybe restored to complete logical and grammatical sentences. These applications may include sentence simplification, machine translation, sentence generation, and text summarization among others. These and other benefits of one or more aspects will become apparent from consideration of the ensuing description.

One of the embodiments provides an agent with a set of words within a sentence or a complete sentence and attributes of which include a model and actions, which can be taken by the agent. The agent is initialized with number of features per word, 128, which is the standard recommendation. The agent is initialized with max words per sentence 20, which is used as an upper limit to constrain the search space. The agent is initialized with a starting index within the input sentence. The starting index may be the pointer that would define an operational window for performing actions to a certain location index within the sentence or on the edges of the sentence.

The agent is initialized with a set of hyperparameters, which includes epsilon ε (ε=1), epsilon decay, ε_decay (ε_decay=0.999), gamma, γ (γ=0.99), and a loss rate η (η=0.001). The hyperparmeter epsilon ε is used to encourage the agent to explore random actions. The hyperparmeter epsilon ε, specifies an ε-greedy policy whereby both greedy actions with an estimated greatest action value and non-greedy actions with an unknown action value are sampled. When a selected random number, r is less than epsilon ε, a random action a is selected. After each episode epsilon ε is decayed by a factor ε_decay. As the time progresses epsilon ε, becomes less and as a result fewer non-greedy actions are sampled.

The hyperparmeter gamma, γ is the discount factor per future reward. The objective of an agent is to find and exploit (control) an optimal action-value function that provides the greatest return of total reward. The standard assumption is that future rewards should be discounted by a factor γ per time step.

The final parameter the loss rate, η is used to reduce the learning rate over time for the stochastic gradient descent optimizer. The stochastic gradient descent optimizer is used to train the convolutional neural network through back propagation. The benefits of the loss rate are to increase performance and reduce training time. Using a loss rate, large changes are made at the beginning of the training procedure when larger learning rate values are used and decreasing the learning rate such that a smaller rate and smaller training updates are made to weights later in the training procedure.

The model is used as a function approximator to estimate the action-value function, q-value. A convolutional neural network is the best mode of use. However, any other model maybe substituted with the convolutional neural network (CNN), (e.g. recurrent neural network (RNN), logistic regression model, etc.).

Non-linear function approximators, such as neural networks with weight θ make up a Q-network which can be trained by minimizing a sequence of loss functions, $L_i(\theta_i)$ that change at each iteration i, $$L_i(\theta_i) = E_{s,a \sim \rho(\cdot)}[(y_i - Q(s,a;\theta)^2)]$$

where $y_i = E_{s,a \sim \rho(\cdot); \acute{s} \sim \xi}[(r + \gamma \max_{\acute{a}} Q(\acute{s}; \Theta_{i-1})|s, a)]$ is the target for iteration i and ρ(s, a) is a probability distribution over states s or in this embodiment sentences s. and actions a such that it represents a sentence-action distribution. The parameters from the previous iteration $\theta_i$ are held fixed when optimizing the loss function, $L_i(\theta_i)$. Unlike the fixed targets used in supervised learning, the targets of a neural network depend on the network weights. Taking the derivative of the loss function with respect to the weights yields, $$\nabla_{\Theta_i} L_i(\Theta_i) = E_{s,a \sim \rho(\cdot); \acute{s} \sim \xi}[(r + \gamma \max_{\acute{a}} Q(\acute{s}; \Theta_{i-1}) - Q(s,a; \Theta_i)) \nabla_{\Theta_i} Q(s,a;\Theta_i)]$$

It is computationally prohibitive to compute the full expectation in the above gradient; instead it is best to optimize the loss function by stochastic gradient descent. The Q-learning algorithm is implemented with the weights being updated after an episode, and the expectations are replaced by single samples from the sentence-action distribution, ρ(s, a) and the emulator ξ.

The algorithm is model-free which means that is does not construct an estimate of the emulator ξ but rather solves the reinforcement-learning task directly using samples from the emulator ξ. It is also off-policy meaning that it follows ε-greedy policy which ensures adequate exploration of the state space while learning about the greedy policy a=$\max_a Q$(s, a; θ).

A CNN was configured with a convolutional layer equal to the product of the number of features per word and the maximum words per sentence, a filter of 2, and a kernel size of 2. The filters specify the dimensionality of the output space. The kernel size specifies the length of the 1D convolutional window. One-dimensional max pooling with a pool size of 2 was used for the max-pooling layer of the CNN. The model used the piecewise Huber loss function and adaptive learning rate optimizer, RMSprop with the loss rate, η hyperparameter.

After the model is initialized as an attribute of the agent, a set of actions are defined that could be taken for each index within an operational window in the sentence. The model is off-policy such that it randomly selects an action when the random number, r [0,1] is less than hyperparmeter epsilon ε. It selects the optimal policy and returns the argmax of the q-value when the random number, r [0,1] is greater than the hyperparmeter epsilon ε. After each episode epsilon ε is decayed by a factor ε_decay, a module is defined to decay epsilon ε. Finally, a module is defined to take a vector of word embeddings and fit a target value.

One of the embodiments provides a way in which to map a sentence to its word-embedding vector. Word embedding comes from language modeling in which feature learning techniques map words to vectors of real numbers. Word embedding allows words with similar meaning to have similar representation in a lower dimensional space. Converting words to word embeddings is a necessary pre-processing step in order to apply machine learning algorithms which will be described in the accompanying drawings and descriptions. A language model is used to train a large language corpus of text in order to generate word embeddings.

Approaches to generate word embeddings include frequency-based embeddings and prediction based embeddings. Popular approaches for prediction-based embeddings are the CBOW (Continuous Bag of Words) and skip-gram model which are part of the word2vec gensim python packages. The CBOW in the word2vec python package on the Wikipedia language corpus was used.

A sentence is mapped to its word-embedding vector. First a large language corpus (e.g. English Wikipedia 20180601) is trained on the word2vec language model to generate corresponding word embeddings for each word. Word embeddings were loaded into memory with a corresponding dictionary that maps words to word embeddings. The number of features per word was set equal to 128, which is the recommended standard. A numeric representation of a sentence was initialized by generating a range of indices from 0 to the product of the number of features per word and the max words per sentence. Finally a vector of word embeddings for an input sentence is returned to the user.

One of the embodiments provides an environment with a current state, which is the current sentence that may or may not have been modified by the agent. The environment is also provided with the POS-tagged current sentence and a reset state that restores the sentence to its original version before the agent performed actions. The environment is initialized with a maximum number of words per sentence.

One of the embodiments provides a reward module that returns a negative reward r− if the sentence length is equal to zero; it returns a positive reward r+ if a grammar built from the sentence is able to parse the sentence and the logical equations derived from the logical language mapper executed by the theorem prover are consistent; and returns a negative reward r− if a grammar built from the sentence is unable to parse the sentence or if the logical equations evaluated by the theorem prover are inconsistent.

At operation, the hypothesis sentence or sentence fragment is provided as input to a reinforcement-learning algorithm a grammar and logical equations are generated in real-time from the hypothesis sentence. The hypothesis sentence, grammatical state, and logical validity represents an environment. An agent is allowed to interact with the sentence and receive the reward. In the present embodiment, at operation the agent is incentivized to perform actions to the sentence that result in grammatically correct and logical sentences.

First a minimum size, batch size, number of episodes, and number of operations are initialized in the algorithm. The algorithm then iterates over each episode from the total number of episodes; for each episode e, the sentence s, is reset from the environment reset module to the original sentence that was the input to the algorithm. The algorithm then iterates over k total number of operations; for each operation the sentence s is passed to the agent module act. A number, r is randomly selected between 0 and 1, such that if r is less than epsilon e, the total number of actions, $n_{total}$ is defined such that $n_{total} = n_a{}^{w_s}$ where $n_a$ is the number of actions and $w_s$ is the index location within the operation window in sentence s. An action a, is randomly selected between a range of 0 and $n_{total}$ and the action a, is returned from the agent module act.

A grammar is generated for the sentence s2 creating a computer program for which the sentence s2 is evaluated. If the grammar parses the sentence a positive grammatical-reward r+ is returned otherwise a negative grammatical-reward r− is returned. A set of logical equations is generated for the discourse s2 creating a computer program for which the discourse s2 is evaluated. If a logical conclusion is inferred from discourse a positive logical-reward r+ is returned otherwise a negative logical-reward r− is returned. A positive total reward is returned if both the grammatical-reward and the logical-reward are positive otherwise a negative total reward is returned. If k, which is iterating through the number of operations is less than the total number of operations a flag terminate is set to False otherwise set flag terminate to True. For each iteration k, append the sentence s, before action a, the reward r, the sentence s2 after action a, and the flag terminate to the tuple list pool. If k<number of operations repeat previous steps else call the agent module decay epsilon, e by the epsilon decay function e_decay.

Epsilon e is decayed by the epsilon decay function e_decay and epsilon e is returned. If the length of the list of tuples pool is less than the min size repeat previous steps again. Otherwise randomize a batch from the pool. Then for each index in the batch set the target=r, equal to the reward r for the batch at that index; generate the word embedding vector s2_vec for each word in sentence 2, s2 and word embedding vector s_vec for each word in sentence, s. Next make model prediction X using the word embedding vector s_vec. If the terminate flag is set to False make model prediction $X_2$ using the word embedding vector s2_vec. Using the model prediction $X_2$ compute the q-value using the Bellman equation: q-value=r+γmax$X_2$ and then set the target to the q-value. If the terminate flag is set to True call agent module learn and pass s_vec and target and then fit the model to the target.

The CNN is trained with weights θ to minimize the sequence of loss functions, $L_i(\theta_i)$ either using the target as the reward or the target as the q-value derived from Bellman equation. A greedy action a, is selected when the random number r is greater than epsilon e. The word embedding vector s_vec is returned for the sentence s and the model then predicts X using the word embedding vector s_vec and sets the q-value to X. An action is then selected as the argmax of the q-value and action a returned.

Reinforcement Learning does not Require Paired Datasets.

The benefits of a reinforcement learning system 110 vs. supervised learning are that it does not require large paired training datasets (e.g. on the order of $10^9$ to $10^{10}$ (Goodfellow I., 2014)). Reinforcement learning is a type of on-policy machine learning that balances between exploration and exploitation. Exploration is testing new things that have not been tried before to see if this leads to an improvement in the total reward. Exploitation is trying things that have worked best in the past. Supervised learning approaches are purely exploitative and only learn from retrospective paired datasets.

Supervised learning is retrospective machine learning that occurs after a collective set of known outcomes is determined. The collective set of known outcomes is referred to as paired training dataset such that a set of features is mapped to a known label. The cost of acquiring paired training datasets is substantial. For example, IBM's Canadian Hansaard corpus with a size of $10^9$ cost an estimated $100 million dollars (Brown, 1990).

In addition, supervised learning approaches are often brittle such that the performance degrades with datasets that were not present in the training data. The only solution is often reacquisition of paired datasets which can be as costly as acquiring the original paired datasets.

From the description above, a number of advantages of some embodiments of the logical sentence length reduction system become evident:

(a) The reinforcement learning grammar-engine is unconventional in that it represents a combination of limitations that are not well-understood, routine, or conventional activity in the field as it combines limitations from independent fields of natural language processing and reinforcement learning.

(b) The reinforcement learning logic-engine is unconventional in that it represents a combination of limitations that are not well-understood, routine, or conventional activity in the field as it combines limitations from independent fields of logic, automated theorem proving and reinforcement learning.

(c) The grammar-engine and logic-engine can be considered a generalizable reward mechanism in reinforcement learning. The limitation of using logical form defined by formal language theory enables generalization across any new environment, which is represented as a discourse in MDP.

(d) An advantage of the logical sentence length reduction system is that it scalable and can process large datasets creating significant cost savings. The calculation provided in the Background section for manually simplifying doctor's notes into patient friendly language shows that such an activity would cost the entire healthcare system $4.8 B per year in USD.

(e) Several advantages of the logical sentence length reduction system applied to simplifying doctors notes into patient friendly language are the following: reduction of healthcare utilization, a reduction in morbidity and mortality, a reduction in medication errors, a reduction in 30-day readmission rates, an improvement in medication adherence, an improvement in patient satisfaction, an improvement in trust between patients and doctors and additional unforeseeable benefits.

INDUSTRIAL APPLICABILITY

A logical sentence length reduction system could be applied to the following use cases in the medical field:

1) A doctor enters a patient's office visit record into the EHR system and clicks on a third-party application containing the logical sentence length reduction system and the input patient record. The doctor then clicks the simplify button. The logical sentence length reduction system would retrieve a storage medium and execute a computer program(s) on a processor(s) and return the content of the patient's office visit record into shorter sentences which would be reviewed by a doctor using the display screen of her workstation. After the doctor completed her review the doctor then forwards the simplified patient note to the patient's electronic healthcare portal. The patient can view the note is his patient portal using the display screen of his Android phone.

2) A patient is diagnosed with melanoma and wants to understand the latest clinical trial for a drug that was recently suggested by her oncologist. The findings of the clinical trial were published in a peer-reviewed medical journal but she is unable to make sense of the paper due to long run-on sentences. She copies the paper into the logical sentence length reduction system and hits the simplify button. The logical sentence length reduction system would retrieve a storage medium and execute a computer program(s) on a processor(s) and return the content of the peer-reviewed medical journal into shorter sentences, which she can view, on the display of her iPad.

Other specialty fields that could benefit from a logical sentence length reduction system include: legal, finance, engineering, information technology, science, arts & music, and any other field that uses jargon.

The invention claimed is:

1. A logical sentence length reduction system, comprising:
    an input sentence;
    a physical hardware device consisting of a memory unit and processor;
    a software consisting of a computer program or computer programs;
    an output sentence;
    a display media;
    the memory unit capable of storing the input sentence created by the physical interface on a temporary basis;
    the memory unit capable of storing the data sources created by the physical interface on a temporary basis;
    the memory unit capable of storing the computer program or computer programs created by the physical interface on a temporary basis;
    the processor is capable of executing the computer program or computer programs;
    wherein one or more processors; and
    one or more programs residing on a memory and executable by the one or more processors, the one or more programs configured to:
        split a sentence into one or a plurality of sentence fragments;
        provide a reinforcement learning system with a sentence fragment as a state;
        provide the reinforcement learning agent with an action or a plurality of actions that are performed on the sentence fragment resulting in a hypothesis sentence;
        provide the reinforcement learning agent with a reward function wherein the reward function determines the logical and grammatical state of the hypothesis sentence and returns a positive reward if the hypothesis sentence is logical and grammatical and a negative reward if the hypothesis sentence is not grammatical and/or not logical;
        wherein the reinforcement learning agent optimizes a policy such that the agent learns modifications to make to the sentence fragment to reconstruct a logical and grammatical sentence;
        wherein the logical sentence length reduction system performs edits on the sentence fragments and produces complete, logical, and grammatical sentences.

2. A reinforcement learning system, comprising: one or more processors; and one or more programs residing on a memory and executable by the one or more processors, the one or more programs configured to:
    perform actions from a set of available actions on a state wherein the state is either a sentence fragment or a sentence;
    constrain actions to an operational window within the state;

wherein the operational window is determined by the location of the sentence break and the location of the noun phrase and verb phrase relative to the sentence break;
select an action to maximize an expected future value of a reward function;
wherein the reward function depends on:
producing a grammatical and logical sentence resulting in a positive reward or producing a non-grammatical sentence and/or an illogical sentence resulting in a negative reward;
wherein an agent optimizes a policy such the agent learns modifications to make within the operation window to rebuild the sentence fragment into a logical, grammatical and complete sentence.

3. The system of claim 2, wherein a grammar engine consisting of a parser that processes input sentences according to the productions of a grammar, wherein the grammar is a declarative specification of well formedness.

4. The system of claim 3, wherein a grammar engine consisting of a parser executes a sentence stored in memory against a grammar stored in memory on a processor and returns the state of the sentence as grammatical or non-grammatical.

5. The system of claim 4, wherein the grammar engine is using a grammar defined in formal language theory such that sets of production rules describe all possible strings in a given formal language.

6. The system of claim 4, wherein the grammar engine can be used to describe all or a subset of rules for any language or all languages or a subset of languages or a single language.

7. The system of claim 4, wherein the grammar engine is executed on a processor in real-time by first executing a part-of-speech classifier on words and punctuation belonging to the input sentence stored in memory on a processor generating part-of-speech tags stored in memory for the input sentence.

8. The system of claim 7, wherein the grammar engine is executed on a processor in real-time by creating a production or plurality of productions that map the part-of-speech tags stored in memory to grammatical rules which are defined by a selected grammar stored in memory.

9. The system of claim 2, wherein a logic engine consisting of an automated theorem prover that processes input sentences according to a set of logical equations derived from a discourse and the hypothesis sentence, wherein the automated theorem prover takes the logical equations as the premise and infers a proof.

10. The system of claim 9, wherein a logic engine consisting of the automated theorem prover executes a logical equation derived from the hypothesis sentence stored in memory against a set of logical equations derived from a discourse stored in memory on a processor and returns the state of the sentence as logical or illogical.

11. The system of claim 10, wherein the logical equations consist of negated relationships that are determined by a symmetrical axis or a plurality of symmetrical axes in a network graph.

12. The system of claim 11, wherein the negated relationships are formulated as a formal logic, such that a set of logical equations is generated.

13. The system of claim 9, wherein the negated relationships are formulated as a first-order logic, such that a set of logic equations is generated.

14. The system of claim 9, wherein the negated relationships are formulated as a second-order logic, such that a set of logic equations is generated.

15. The system of claim 9, wherein the negated relationships are formulated as a higher-order logic, such that a set of logic equations is generated.

16. The system of claim 9, wherein the logic engine evaluates the hypothesis sentence at a local contextual level, wherein the local contextual level consists of neighboring word or words, character or characters, number or numbers, word group or word groups, sentence or sentences, paragraph or paragraphs, document or documents are used in isolation or in combination to construct a set of logical equations.

17. The system of claim 9, wherein the logic engine evaluates the hypothesis sentence at a global semantic level, wherein the global semantic level consists of neighboring word or words, character or characters, number or numbers, word group or word groups, sentence or sentences, paragraph or paragraphs, document or documents used in isolation or in combination which share a common word, character, or numerical with the hypothesis sentence.

18. The system of claim 9, wherein the logic engine returns a positive reward to the agent if the symbolic equations describing the sentence are consistent at a local contextual level and at a global semantic level and a negative reward to the agent if the symbolic equations describing the sentence are inconsistent at either a local contextual level or at a global semantic level.

19. The method for reinforcement learning system, comprising the steps of:
performing actions from a set of available actions;
performing actions on a state, a sentence fragment, or a sentence;
restricting actions performed by an agent to an operational window;
wherein the operational window is determined by the location of the sentence break and the location of the noun phrase and verb phrase relative to the sentence break;
selecting an action to maximize an expected future value of a reward function, wherein the reward function depends on:
producing a grammatical and logical sentence resulting in a positive reward or producing a non-grammatical sentence and/or an illogical sentence resulting in a negative reward;
wherein an agent optimizes a policy such the agent learns modifications to make within the operation window to rebuild the sentence fragment into a logical, grammatical and complete sentence.

* * * * *